United States Patent [19]

Nazari

[11] Patent Number: 5,554,183
[45] Date of Patent: Sep. 10, 1996

[54] VASCULAR PROSTHESIS FOR THE SUBSTITUTION OR INTERNAL LINING OF BLOOD VESSELS OF MEDIUM OR LARGE DIAMETER AND DEVICE FOR ITS APPLICATION

[76] Inventor: Stefano Nazari, Via Bignanico 12/C, 22100 Como, Italy

[21] Appl. No.: 372,746

[22] Filed: Jan. 13, 1995

[30] Foreign Application Priority Data

Jan. 19, 1994 [IT] Italy .................. MI94A0066

[51] Int. Cl.⁶ ........................................ A61F 2/06
[52] U.S. Cl. ........................................ 623/1; 604/96
[58] Field of Search ............ 623/1, 12; 604/96, 604/104–107; 606/108, 140, 157, 158, 198, 194, 191

[56] References Cited

U.S. PATENT DOCUMENTS

| | | | |
|---|---|---|---|
| 4,140,126 | 2/1979 | Choudhury | 623/1 |
| 4,592,355 | 6/1986 | Antebi | 606/157 |
| 4,710,192 | 12/1987 | Liotta et al. | 623/1 |
| 4,885,003 | 12/1989 | Hillstead | 604/107 |
| 4,998,539 | 3/1991 | Delsanti | 606/194 |
| 5,222,971 | 6/1993 | Willard et al. | 606/158 |
| 5,383,887 | 1/1995 | Nadal | 606/198 |

FOREIGN PATENT DOCUMENTS

| | | |
|---|---|---|
| 0544485 | 6/1993 | European Pat. Off. . |
| 2805749 | 8/1978 | Germany . |
| 93/017636 | 9/1993 | WIPO ................. 623/1 |

*Primary Examiner*—Michael J. Milano
*Attorney, Agent, or Firm*—Guido Modiano; Albert Josif

[57] ABSTRACT

Vascular prosthesis for the substitution or internal lining of blood vessels of medium and large diameter and to a device for its application which includes a tubular body of biocompatible material that is associated with, at least at one longitudinal end, at least one body at annular development, that is disposed substantially coaxial to the tubular body and that is radially expandable for the engagement of the tract of the tubular body, which contains the body at annular development, against the inner walls of a blood vessel proximal to the segment of the vessel to be substituted, or internally lined, with the prosthesis. The body at annular development includes at least one loop of at least one wire elastically flexible, which is slideably mounted on a support associated to a lateral portion of the tubular body. This wire is slideable with respect to the support mentioned before to vary the amplitude of the loop and tools are predisposed to contrast the wire sliding in respect to the support in order to maintain the expansion or contraction, given to the loop by means of the controlled sliding of the wire relatively to the support, at ceasing of the force generating the sliding.

23 Claims, 6 Drawing Sheets

VASCULAR PROSTHESIS FOR THE SUBSTITUTION OR INTERNAL LINING OF BLOOD VESSELS OF MEDIUM OR LARGE DIAMETER AND DEVICE FOR ITS APPLICATION

BACKGROUND OF THE INVENTION

The present invention consists of a vascular prosthesis for the substitution or internal lining of blood vessels of medium and large diameter and of a device for its application.

Aneurysms of various origin and traumatic lesions are the most frequent conditions requiring thoracic and abdominal aortic prosthetic substitution. Current techniques include the surgical exposure of the aortic segment to be replaced; both ends of the aneurysm are isolated and clamped to stop the blood flow; the vessel is opened and a tubular conduit of biocompatible material is interposed and manually sutured at both ends.

Most complications of descending thoracic aorta prosthetic substitution (paraplegia, liver and renal injury) are due to ischemic lesion of distal organs (spinal cord, liver and kidney) during the blood flow interruption phase and the incidence is proportional to the duration of said phase. Other complications are related to the manoeuvres taken to compensate the haemodynamic modifications induced by clamping (extracorporeal circulation, heparinization, etc.).

A further source of complications is the suture line which can bleed at the operative table or cause pseudoaneurysm in the late postoperative period; these problems are enhanced by alterations of the aortic wall due to the primary disease.

SUMMARY OF THE INVENTION

The main aim of this invention is to solve these problems using a vascular prosthesis that can be applied very quickly greatly reducing the duration of the interruption of the blood flow in the segment to be substituted.

Within the above aim, an object of the invention is that of realizing a prosthesis that can be applied also without blood flow interruption.

Another aim of the invention is that of realizing a prosthesis that can be applied without necessarily requiring the surgical exposition of the blood vessel.

Another aim of the invention is to realize a prosthesis that can be applied to the vessel without surgical suture.

A further aim is that of realizing a device that would allow the positioning and the application of the vascular prosthesis, as invented, without interruption of the blood flow in the substituted vascular segment.

This aim and these and other objects which will become apparent hereinafter are achieved by a vascular prosthesis for the substitution or internal lining of blood vessels of medium and large diameter characterized by the fact of comprising a tubular body of biocompatible material associated, in proximity of at least one of its longitudinal ends, with at least one annular shaped body disposed substantially coaxial to said tubular body and which can be radially expanded for engagement of the portion of said tubular body, containing said annular shaped radially extendable body, against the internal walls of a blood vessel proximal to the segment to be substituted or internally lined, with the prosthesis, said annular shaped body being constituted of at least one loop of at least one wire elastically flexible slidingly mounted on a support associated to a lateral portion of said tubular body, said wire being slideable with respect to said support in order to vary the size of said loop, contrasting means of the sliding of said wire relative to said support being provided in order to maintain the expansion or contraction given to said loop by the controlled sliding of said wire relative to said support, when the force that generated it ceases.

For the application of the vascular prosthesis according to the invention, when one desires to operate without blood flow interruption, a device is preferably used, characterized in that it comprises a flexible tubular support that can be inserted into the lumen of a blood vessel distal of the segment to be substituted, or internally lined, with said prosthesis, said tubular support being provided, at its distal end, intended to be inserted into the blood vessel, with retaining means of said support and, at its proximal end, intended to be sited externally of said vessel, with controlling means which are connected, by connection means sliding internally of said tubular support, to said at least one wire for its sliding relative to said support for a variation of the size of said at least one loop for the radial expansion or contraction of said annular shaped body, deactivation means of said retaining means of said support being provided and said connecting means being releasable at command by said at least one wire in order to leave the prosthesis in the vessel after its application.

BRIEF DESCRIPTION OF THE DRAWINGS

Further features and advantages of the invention will be apparent from the following description of a preferred, though not exclusive embodiment of the vascular prosthesis according to the invention, as well as of a device for its application, illustrated in the accompanying illustrative, not limitative drawings wherein.

DESCRIPTION OF THE PREFERRED EMBODIMENTS

With reference to the cited figures, the vascular prosthesis according to the invention, indicated generally by the reference numeral 1, comprises a tubular body 2 made of synthetic biocompatible material, for example with materials commercially known as Dacron or Teflon, that is associated, at at least one of its longitudinal ends, with at least one annular shaped body 3 which is disposed substantially coaxial to the tubular body 2 and which is radially expandable in order to engage the portion of the tubular body 2, which contains the annular shaped, expandable body 3, against the inner walls of a blood vessel 4 proximal to the segment of the vessel to be substituted, or internally lined, with the prosthesis.

According to the invention, the annular shaped, expandable body 3 consists of at least one loop 5, 6 of a wire 7, 8 which is elastically flexible and which is slidingly mounted on a support 9 associated to a lateral portion of the tubular body 2 parallel to the axis 2a of tubular body 2. The wire 7, 8 slides relative to the support in order to vary the size of loop 5, 6 or to radially increase or decrease the volume of the portion of tubular body 2 that contains the loop 5, 6, and means are provided to contrast the sliding of wire 7, 8 relative to the support 9, in order to maintain the expansion or contraction given to the loop 5, 6 by the controlled sliding of wire 7, 8 relative to the support 9, when the force that generated it ceases.

Preferably two wires 7, 8, in harmonic stainless steel are provided, which each describes a double loop, respectively 5 and 6 and each of these double loops presents: a first tract 5a, 6a which extends out of the support 9 in a direction which is inclined in respect to an imaginary plane transversal to the axis 2a of the tubular body 2, a second annular shaped section 5b, 6b, a second and a third tract forming a substantially annular loop section, which is bound to the support 9 in an area that is distanced from the area from which the first tract 5a, 6a extends, and which develops in a plane which is substantially perpendicular to the axis 2a of the tubular body 2, and a third tract 5c, 6c that re-enters into the support 9 in an area that is proximal to the area from which the first tract 5a, 6a extends.

Preferably, the support 9 extends longitudinally, along its axis, between a first and a second longitudinal end thereof, its axis being substantially parallel to the axis of the tubular body. The support preferably has a plurality of lateral holes, including at least a first lateral hole and a second lateral hole proximal to said first lateral hole, and at least a third lateral hole and a fourth lateral hole proximal to the third hole, the third and fourth holes being longitudinally spaced with respect to the first and second holes. A wire enters the support through the first longitudinal end thereof, coming then out of the support through the first lateral hole and reentering the support through the third lateral hole so as to define a first tract of wire inclined with respect to a plane perpendicular to the axis of the tubular body and a second tract of wire in a plane perpendicular to the axis of the tubular body, the wire (7,8) further coming out again of the support through the fourth lateral hole and reentering the support through the second lateral hole so as to define a third tract of wire substantially in the same plane as the second tract, and a fourth tract of said wire inclined with respect to a plan perpendicular to the axis of said tubular body, the second tract and the third tract forming substantially an annular loop, the wire coming out then of the support through the first longitudinal end thereof, thereby expansion and contraction of the tubular body is obtained when the wire slides with respect to the support.

The support 9 is preferably constituted by a substantially cylindrical, preferably hollow, body and wires 7, 8 extend laterally from the support 9 to make double loops 5, 6.

Appropriately, the double loops 5, 6 are spaced one from the other in a direction which is parallel to the axis 2a of the tubular body 2, or in direction parallel to the axis 9a of the support 9, spacing between each other the holes through which the wire 7, 8 laterally extend from the support 9.

It should be noted that the connection of the section 5b, 6b of the loops 5, 6 to the support 9 is obtained by multiple passages of the wire 7, 8 which make the loops 5, 6 through the support 9 in a position which is appropriately spaced from the position of the holes through which wires 7, 8 extend from support 9 so that the section 5b, 6b of the loops is maintained in a plane which is substantially perpendicular to the axis 2a of the tubular body 2 without significant variation during use.

The contrasting means of the sliding of the wires 7, 8 relative to the support 9, to maintain the given radial expansion or contraction of the loops 5, 6, is constituted by the friction resulting from the passage through the support 9 by the wires 7, 8. This friction, which derives from the dimension and configuration of the holes defined in the support 9 and through which the wires 7, 8 pass, as well as from the material constituting the support 9 in relation with the material from which the wires 7, 8 are made, can however provide a sufficient resistance to undesired accidental contraction or expansion of the loops 5, 6.

Advantageously means are provided for the positioning of one of the double loops 5 in respect to the other loop 6. These positioning means comprise wire segments 10, also made of harmonic stainless steel, that connect the annular loop section 5b of the loop 5 and the annular loop section 6b of the loop 6 one with the other in such a way that they effectively contrast the deflection of the second section 5b, 6b of the loops and maintain them in planes substantially parallel to each other and substantially perpendicular to the axis 2a of the tubular body 2.

The ends of the wires 7 and 8 that constitute the loops 5 and 6 extend out of an axial end of the support 9 and are associated integrally with a manoeuvre cylinder block 11 that is mobile at command relatively to the support 9 to cause the sliding of wires 7, 8 to obtain a variation in the size of the loops 5 and 6.

More particularly, the four ends of the wires 7 and 8 are connected to the manoeuvre cylinder block 11 by previously inserting them in a sleeve 12, screw-threaded externally, that has just sufficient room to contain the four ends of the wires 7 and 8, and once the wires have passed through the sleeve 12, refolding the ends of wires 7 and 8, so that their extraction from the sleeve 12 is prevented. The sleeve 12 is coupled with a screw-threaded seat 13 realized at one end of the manoeuvre cylinder block 11, preferably having a substantially cylindrical shape. At the other end of the manoeuvre cylinder block 11 there is a cavity 14, delimited by a diaphragm 15 that separates it from the screw-threaded seat 13.

The loops 5, 6 of the wire 7, 8 and at least the portion of the support 9 which is affected by the loops 5, 6 are connected, for example by repeated crossing passages, to a first portion 16 of the tubular body 2 that consists preferably of a segment of prosthesis of fabric annularly disposed so that the folds usually present in these fabrics are parallel to the axis 2a and hence radial contraction and expansion of this portion 16 is facilitated. This first portion 16 is associated, for example by a suture, to the axial end of a second substantially cylindrical portion 17 which is substantially coaxial to the first portion 16 in its annular arrangement.

The manoeuvre cylinder block 11 and the portion of the wires 7, 8 that extend from manoeuvre cylinder block 11 to the support 9 are disposed externally of the tubular body 2.

The device for the application of the prosthesis according to the invention, indicated generally by the reference numeral 20, comprises a flexible tubular support, or sheath 21, that is insertable into the lumen of a blood vessel 4 distal to the section to be substituted, or internally lined, with the prosthesis 1. This tubular support 21 is provided, at its distal end, that is intended to be inserted into the blood vessel 4, with retaining means of the support 9 and, at the proximal end that is intended to be sited externally of the vessel 4, with control means that are connected, through connecting means that can slide inside the tubular support 21, to wires 7 and 8 to cause them to slide relative to the support 9.

Figures 1, 2, 4:
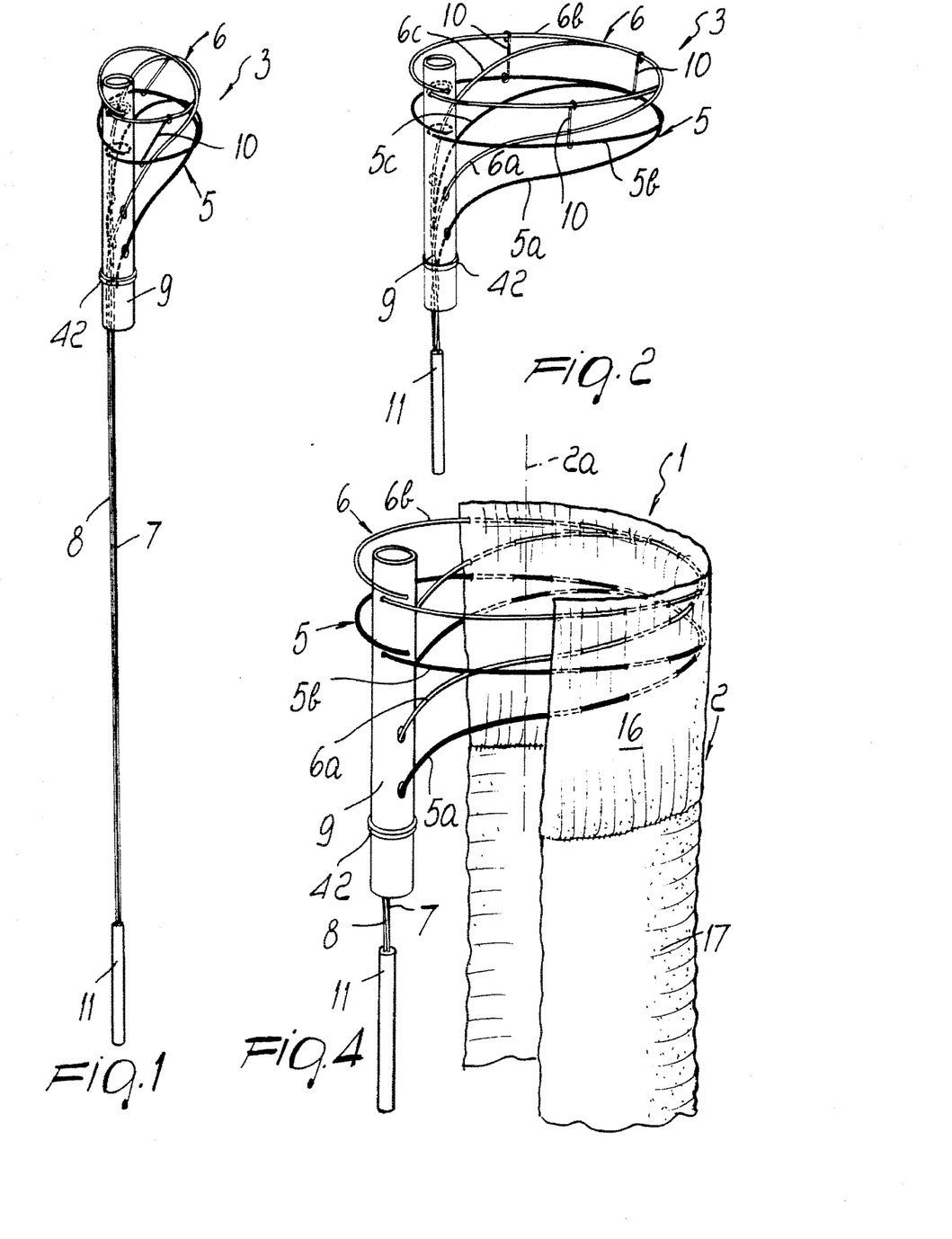
FIG. 1 is a perspective view of the annular shaped body of the prosthesis according to the invention in a radially contracted position.
FIG. 2 is a perspective view of the annular shaped body of the prosthesis according to the invention in a radially expanded position.
FIG. 4 is an enlarged and partially in section view of a detail of the prosthesis according to the invention.
Figures 3, 5, 6, 7:
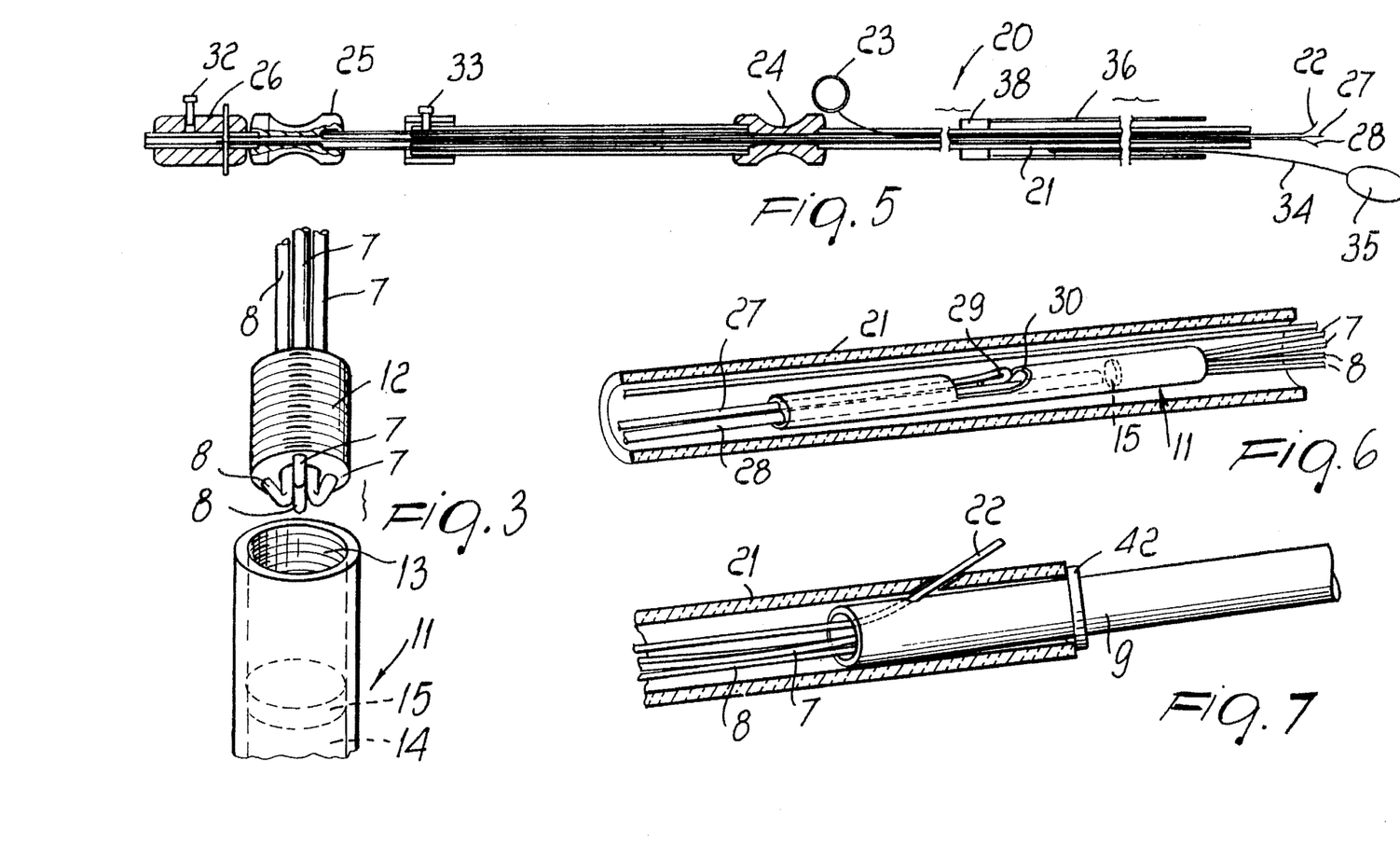
FIG. 3 is an enlarged and exploded view of a detail of FIGS. 1 and 2.
FIG. 5 is a schematic axial section of the device for the application of the prosthesis according to the invention.
FIG. 6 is an enlarged, perspective and partially in section view of the device for the application of the prosthesis according to the invention.
FIG. 7 is an enlarged, perspective and partially in section view of the device.

The retaining means of the support 9 include, appropriately, a retaining cable 22 which is slideable inside the tubular support 21 and that passes through predisposed holes made in the distal end of the tubular support 21 and in the end section of the support 9 that is appropriately inserted inside the distal end of the tubular support 21; in this way the retaining cable 22, by passing through both the support 9 and the tubular support 21, connects these two members one to the other, contrasting the axial sliding of one in respect to the other, as shown in detail in FIG. 7. The axial sliding of the support 9 in direction of the tubular support 21 can be further contrasted by a beat ring 42 in an area of the support 9 proximal to its end to be inserted in the tubular support 21.

The other end of the retaining cable 22 extends out of the tubular support 21, into its area close to its proximal end and therefore, during the operation, it lies externally of the blood vessel 4, and it is provided with a ring 23 by which it is possible to cause sliding of the retaining cable 22 with respect to the tubular body 21 in the direction that causes the release of such cable from the support 9 and from the tubular support 21 thus releasing the support 9 from the tubular support 21.

Appropriately in proximity to the ring 23, on the tubular support 21, a gripping area 24 is provided to facilitate the traction operation of the retaining cable 22.

To cause the sliding of the wires 7 and 8 relative to the support 9, the control means include a first handle 25 and a second handle 26 that are sited at the proximal end of the tubular support 21 and are connected to the manoeuvre cylinder block 11 by a first cable 27 and a second cable 28 that slide inside the tubular support 21 following the axial movement of the handles 25 and 26 in respect to tubular support 21.

More particularly, the first cable 27 presents, at its distal end, i.e. the opposite end with respect to the handle 25, a folding 29 which brings its entire volume equal to twice the diameter at this folding 29. The first cable 27 is inserted into the end of the manoeuvre cylinder block 11 opposite the end where the sleeve 12 is inserted and the folding 29 is sited at a slot 30 prepared in an intermediate area of the lateral surface of the manoeuvre cylinder block 11. The cavity 14 presents, from the inserting end of the first cable 27 to the slot 30, a lumen equal to nearly twice the diameter of the first cable 27, so that the first cable 27 can be inserted and removed in the manoeuvre cylinder block 11 despite the presence of the folding 29. After insertion of the first cable 27, the second cable 28 is inserted in the manoeuvre cylinder block 11 from the same end of insertion as the first cable 27 and, with its presence, prevents extraction of the first cable 27.

The two handles 25 and 26 can, integrally one with the other, slide axially relative to the tubular support 21 so as to operate the axial sliding of the manoeuvre cylinder block 11 in respect to support 9 held at the distal end of the tubular support 21 to cause a variation in the size of the loops 5 and 6, or they can slide one in respect to the other so as to allow the release of the second cable 28 from the manoeuvre cylinder block 11 and hence the release of the first cable 27 from the manoeuvre cylinder block 11 so as to release the manoeuvre cylinder block 11 from the tubular support 21 when the prosthesis is to be left in the blood vessel.

The first handle 25 presents, appropriately, an extension 31 which extends inside the handle 26 and can be blocked by a screw 32, so as to render the handle 25 and 26 integral one with the other, or to release one handle from the other as required.

Moreover, on the proximal end of the tubular support 21 a screw 33 is provided that allows sliding of the first handle 25 relative to the tubular support 21 to be blocked.

Advantageously, prosthesis guiding means are provided inside the blood vessel. Such guiding means include a cable guide 34 that is connected with one of its ends to the tubular support 21 and that axially crosses the tubular body 2 of the prosthesis 1. The end of this cable guide 34, opposite to its end connected to the tubular support 21, is provided with an ogival body 35.

The tubular support 21 is mounted in an axially sliding way and haematically-sealed, inside a tube 36 that is partially insertable inside the vessel or in a branch that can be closed around the tube 36, for example by a ligature 37, so as to obtain haematic sealing during the insertion of the prosthesis 1 into the vessel 4.

The seal between the tubular support 21 and the tube 36 can be obtained by positioning inside the tube 36 a disk gasket 38 which is crossed by the tubular support 21.

In order to avoid blood loss externally, seal disks 48 are provided also between the internal surface of the tubular support 21 and the cables 22, 27 and 28.

Advantageously means for anchoring the tubular body 2 of the prosthesis to the lateral surface of the tubular support 21 during insertion are also provided. Such anchoring means include an eyelet 39 that can be obtained by a length of suture thread, that is connected to the tubular body 2 of the prosthesis in proximity to its end opposite to the section 16 and that can be inserted in a predisposed slot 40 made in the lateral surface of the tubular support 21 at the passage of the retaining cable 22, so that the retaining cable 22 also passes through the eyelet 39 so causing the lateral anchoring of the prosthesis that can be left in site by the partial extraction of the retaining cable 22 from the tubular support 21, as illustrated in detail in FIG. 13 and 15.

The application of the prosthesis according to the invention with the device described above is carried out as follows.

First of all the ogival body 35 is passed axially through the prosthesis with its first portion 16 suitably dilated.

Then the prosthesis 1 is disposed in conditions of minimum volume around its axis 2a by manually moving the manoeuvre cylinder block 11 as far away as possible from the support 9, so that the loops 5 and 6 are maximally contracted. The manoeuvre cylinder block 11 is then blocked to the end of the first cable 27 by placing the folding 29 at the slot 30 and by inserting the second cable 28 into the cavity 14 so that this cable 28 keeps the first cable 27 blocked in the manoeuvre cylinder block 11. At this point the manoeuvre cylinder block 11 is inserted into the distal end of the tubular support 21 until an end section of the support 9 also results inserted in the distal end of the tubular support 21. The support 9 is then blocked to the tubular support 21 by the insertion, through the support 9 and through the flexible support 21, of the end of the retaining cable 22. During the insertion operation of the retaining cable 22, the eyelet 39 sited in proximity of the proximal end of the prosthesis, is inserted into the slot 40 and the same retaining cable 22 passes through. In this way the prosthesis is still anchored to the distal end of the tubular support 21 and the section 17 of the tubular body 2 is wrapped around the tubular support 21.

At this point the tubular support 21 is inserted into a vessel 4 distally of the area of the vessel to be substituted, or internally lined, with the prosthesis 1, or inside a lateral branch of that vessel, so as to allow the positioning of the tube 36 at an area of the vessel that can be tightened around the tube 36 so as to produce an haematic seal. Subsequently, acting on the tubular support 21, its sliding relative to the tube 36 is caused so as to push the prosthesis along the vessel 4, as shown in detail in FIGS. 12 and 13. The advance of the prosthesis along the blood vessel can be radiologically controlled in order to obtain the correct positioning of the prosthesis with the section 16 proximal to the segment of the vessel to be substituted, or internally lined, with the prosthesis.

Figure 8:
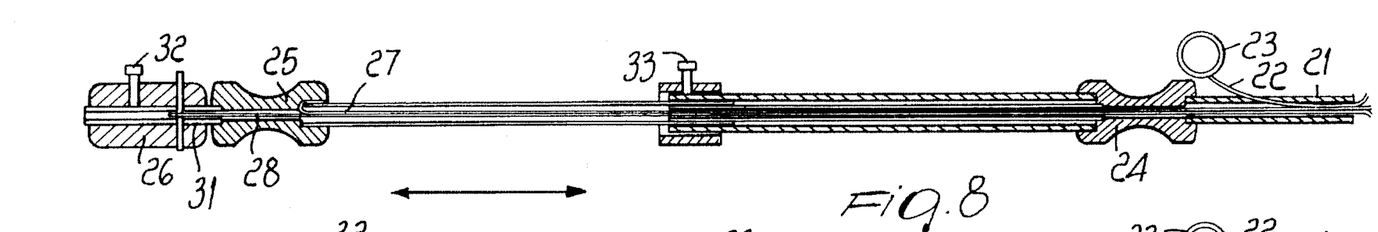
FIGS. 8 to 11 illustrate the device in proximity to its proximal end in different functioning conditions.
Figure 9:
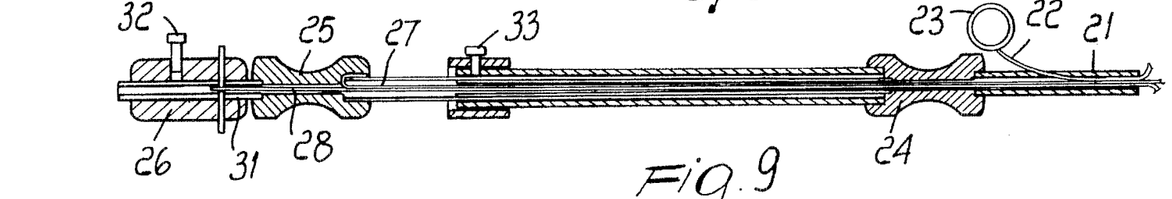
Figure 10:
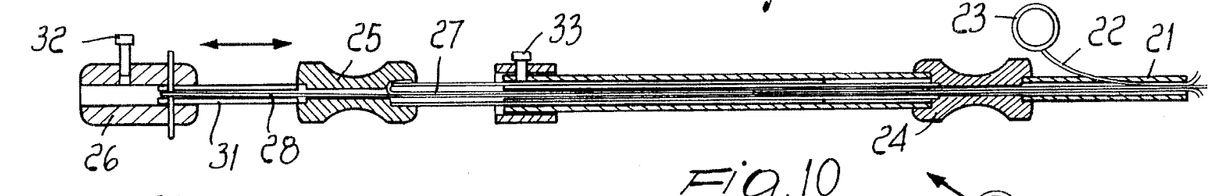
Figure 11:
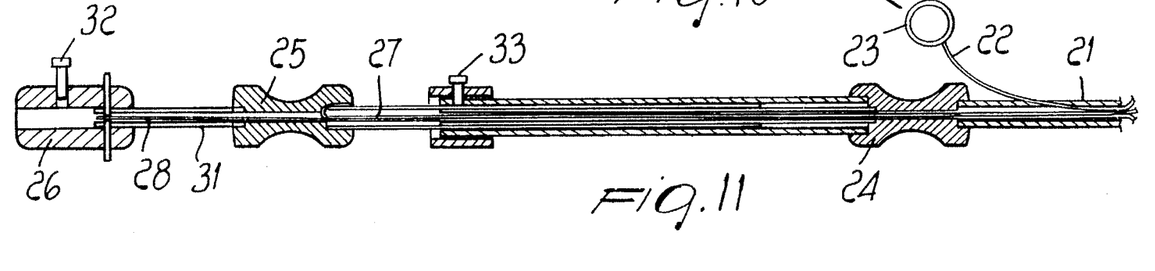
Figures 12, 14, 15:
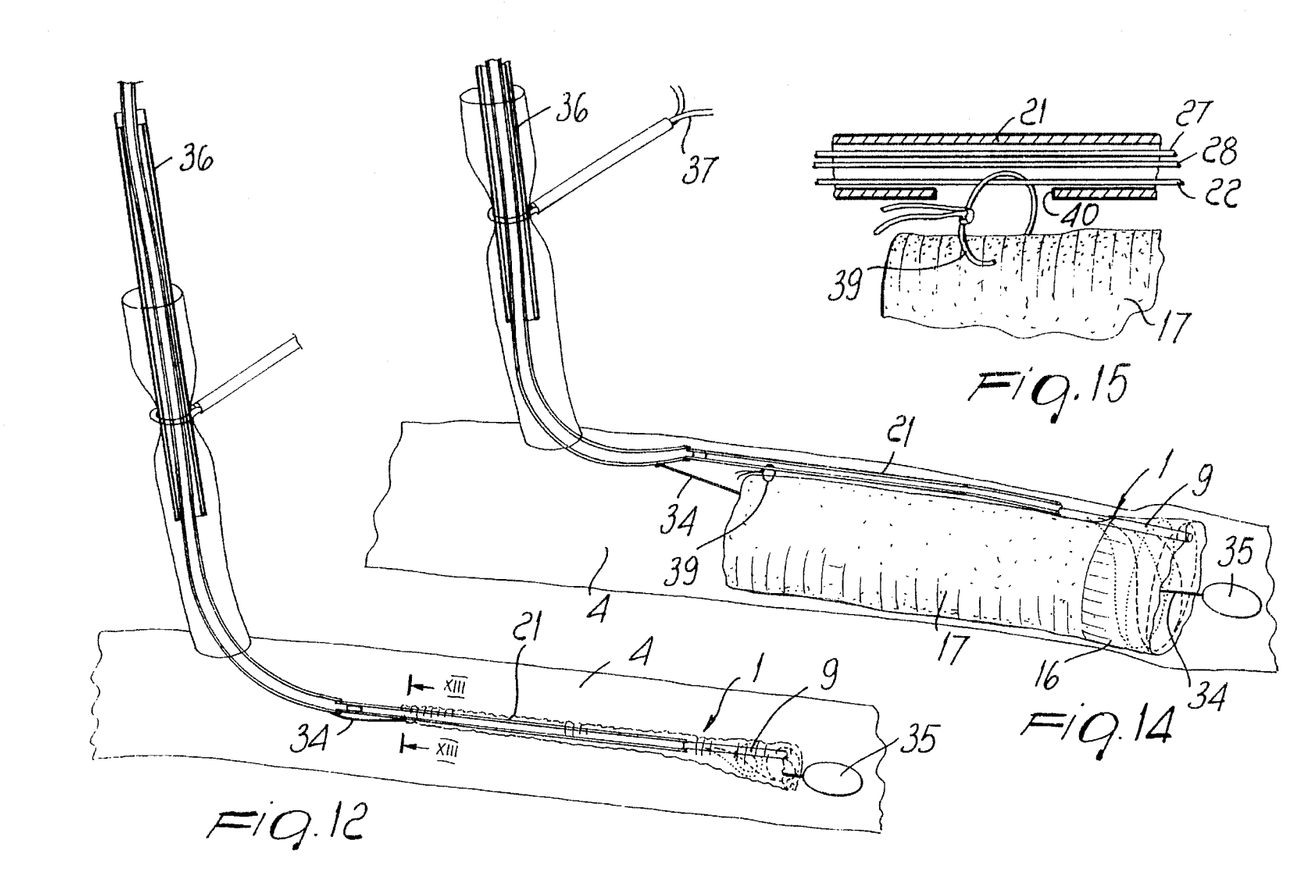
FIG. 12 is a schematic view of the insertion of the prosthesis into a blood vessel according to the invention.
FIG. 14 illustrates the radial expansion phase of the annular shaped body of the prosthesis inside the blood vessel.
FIG. 15 is an enlarged view of a detail of FIG. 14.
Figures 13, 16:
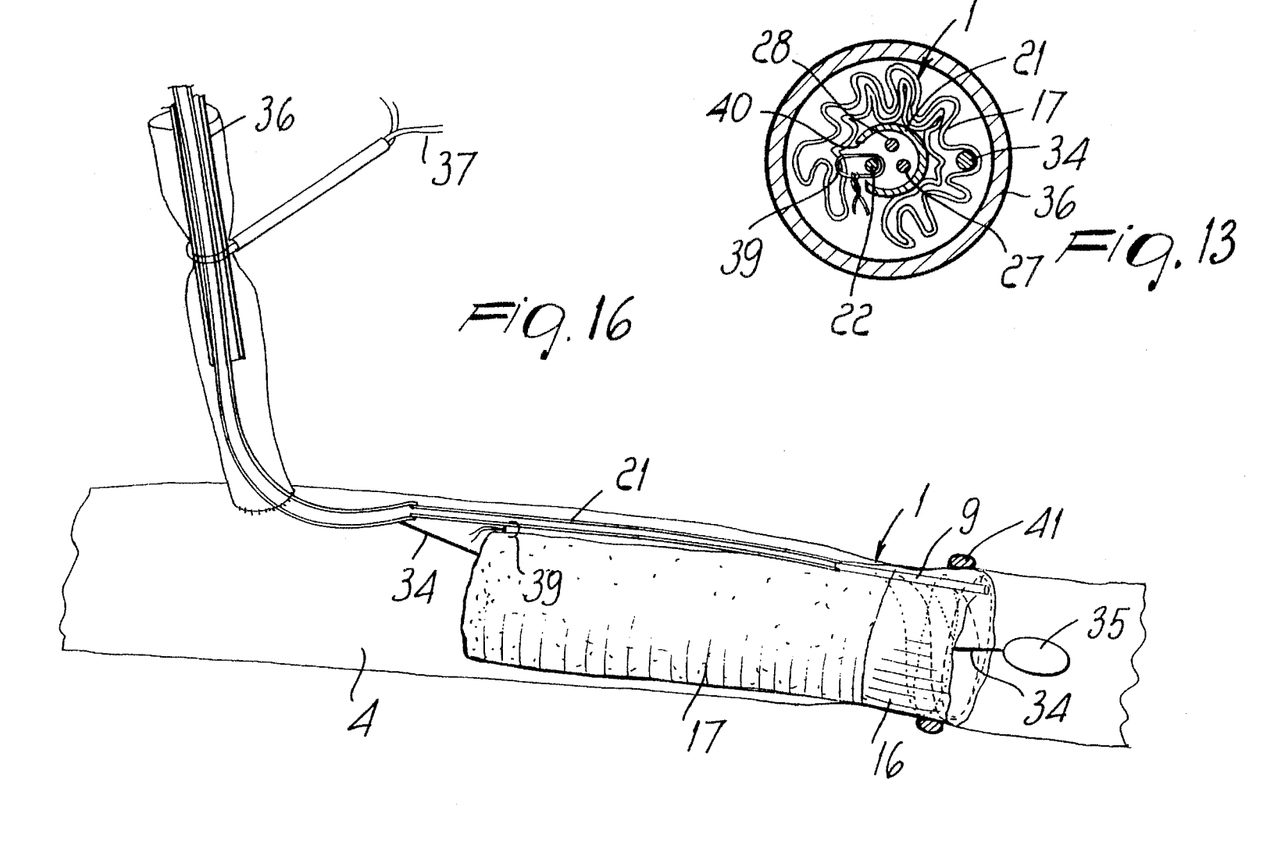
FIG. 13 is an enlarged section of FIG. 12 taken along the axis XIII—XIII.
FIG. 16 is a view of the device and the prosthesis after being applied.

When the prosthesis is correctly positioned, the handles 25 and 26 integral one with the other by the screw 32 are actioned in order to push the cables 27 and 28 along the tubular support 21 in the direction that causes the dilatation of the loops 5 and 6 and then achieves adhesion of the prosthesis to the internal walls of the blood vessel (FIGS. 8,9,14). When the degree of radial expansion of the portion 16 of the prosthesis is such that a seal between the prosthesis and vascular wall is achieved, the tubular support 21 is released from the prosthesis. This release is achieved by unscrewing the screw 32 so that the handle 26 is separated from the handle 25 and then by partially sliding the second cable 28 and then the first cable 27 so as to release these cables from the manoeuvre cylinder block 11; finally the retaining cable 22 is partially slid causing the release of the support 9 and at the same time the release of the eyelet 39. In this way, the device for the application of the prosthesis is completely released from the prosthesis itself and can be removed from the blood vessel.

It should be noted that at anytime during the operation, acting on the handle 25 and 26 in reverse so as to cause a reduction of the loops 5 and 6 to minimum size, it is possible to correct the prosthesis position inside the vessel or to remove the prosthesis completely.

Whenever the vessel to be substituted, or internally lined, with the prosthesis is surgically exposed it is possible to increase the adhesion of the portion 16 with the vessel walls by tying a ligature around the vessel at the expanded portion 16.

When the tract of the vessel is surgically exposed and clamped, the prosthesis can be manually positioned by actioning, instead of the illustrated device, directly on the wires 7 and 8 to achieve dilatation of the loops 5b and 6b that engage the prosthesis against the vessel internal walls.

Figure 17:
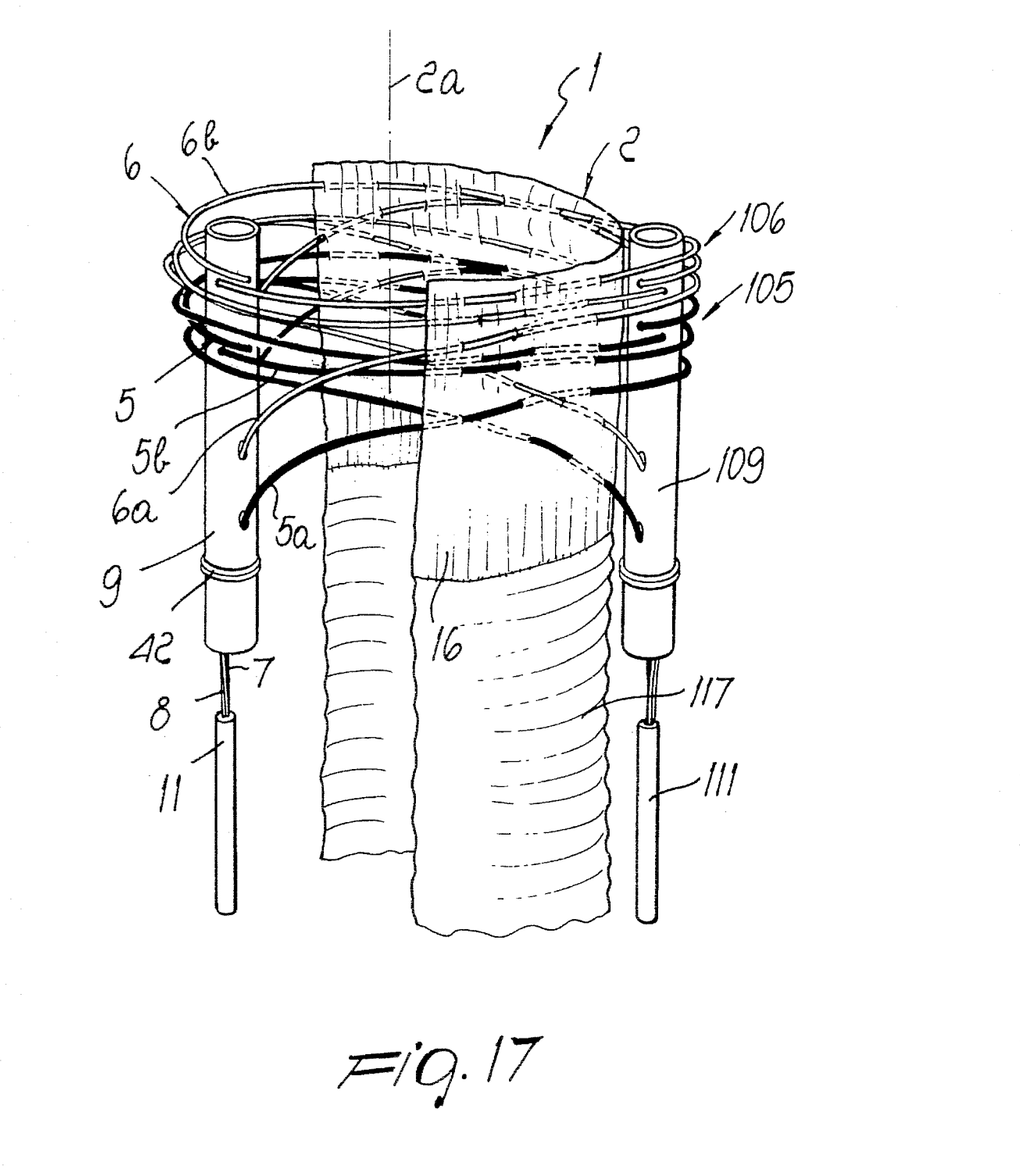
FIG. 17 is a partially sectioned perspective view of another embodiment of the prosthesis according to the invention.

As shown in FIG. 17, in order to improve the balance of the forces that act on the vessel it is advantageous to predispose a second support 109, realized substantially as the support 9, and positioned in an area diametrically opposite to the support 9 externally of the tubular support 2. The support 109 contains one or more wires 105, 106 with loops disposed substantially as the loops of the wires 5 and 6 and connected to another manoeuvre cylinder block 11. Also the loops of wires 105 and 106 are connected to portions of the tubular body 2, as already described in reference to the loops of wires 5 and 6. The expansion of the loops 105 and 106 will be obtained by a device as described, or by a similar device, with two first cables 27 and two second cables 28.

Moreover an annular body 3 can be provided which is similar to that already described, also at the other axial end of the tubular body 2.

In practice it has been observed that the prosthesis according to the invention realizes the prefixed aim, since it allows the substitution, or the inner lining, of a vascular segment to be carried out, significantly reducing the blood flow interruption phase; moreover when the device for endovascular application is used there is no blood flow interruption phase at all, thus preventing paraplegia due to spinal cord ischemic necrosis, kidney and liver ischemic damage, without requiring by-pass or extracorporeal circulation between the proximal and distal vascular areas and without systemic heparinization, required when extracorporeal circulation is used.

Although the prosthesis according to the invention as well as the device for its application are intended in particular for descending thoracic aorta substitution in case of aneurysms, or dissection, also in rupture phase, and in case of traumatic aortic laceration, it could be advantageously used also for the prosthetic substitution of any section of artery or vein the lumen of which is at least partially patent.

Although the prosthesis according to the invention and the device for its application were prepared for the treatment of aneurysms and traumatic rupture of the thoracic aorta that can be used advantageously also for the prosthetic substitution of any section of artery or vein the lumen of which is at least partially patent.

The prosthesis according to the present invention, as well as the device for its application are susceptible to numerous modifications and variations, all falling within the scope of the inventive concept; furthermore all details may be substituted by technically equivalent elements.

In practicing the invention any size or material may be used, providing that they are compatible with the specific use, according to the contingent requirements and the state of the art.

What is claimed is:

1. Vascular prosthesis for substitution or internal lining of a segment of a blood vessel of medium or large diameter, comprising a tubular body made of biocompatible material, said tubular body defining a lateral wall, a first and a second longitudinal end thereof and a longitudinal axis thereof;

at least one radially expandable body disposed substantially coaxial to said tubular body and perimetrically connected to said tubular body, said expandable body comprising a support extending longitudinally along an axis between a first and a second longitudinal end thereof, said axis being substantially parallel to the axis of the tubular body, said support having a plurality of lateral holes, said plurality of lateral holes including at least a first lateral hole and a second lateral hole proximal to said first lateral hole, and at least a third lateral hole and a forth lateral hole proximal to said third hole, said third and fourth holes being longitudinally spaced with respect to said first and second holes; and at least one elastically flexible wire slidingly mounted on said support for radial expansion and contraction of said expandable body, said wire entering the support through said first longitudinal end thereof, said wire then coming out from the support through said first lateral hole and reentering the support through said third lateral hole so as to define a first tract of said wire inclined with respect to a plane perpendicular to said axis of said tubular body and a second tract of said wire in a plane perpendicular to said axis of said tubular body, said wire further coming out again from the support through said forth lateral hole and reentering the support through said second lateral hole so as to define a third tract of said wire substantially in the same plan as the second tract, and a forth tract of said wire inclined with respect to a plan perpendicular to the axis of said tubular body, said second tract and said third tract forming substantially an annular loop, said wire coming out then from the support through said first longitudinal end thereof, thereby expansion and contraction of said tubular body is obtained when said wire slides with respect to said support, said wire being frictionally engaged to said support in said first, second, third and fourth lateral hole, said expandable body being connected to said tubular body by repeated passages of said wire along said first, second, third and forth tract through the wall of said tubular body, thereby a radial expansion of said tubular body is obtained when said expandable body is expanded, said expandable body being disposed at said first end of said tubular body.

2. Vascular prosthesis, according to claim 1, wherein said expandable body comprises at least two wires, each of said at least two wires defining a first tract of said wire inclined with respect to a plane perpendicular to said axis of said tubular body, a second tract of said wire in a plane perpendicular to said axis of said tubular body, a third tract of said wire substantially in the same plan as the second tract, and a forth tract of said wire inclined with respect to a plan perpendicular to the axis of said tubular body, said second tract and said third tract forming substantially an annular loop, said first, second, third and forth tracts of said first wire being longitudinally spaced from and substantially parallel to said first, second, third and forth tracts of said second wire.

3. Vascular prosthesis, according to claim 2, comprising means for positioning said first wire in respect to said second wire.

4. Vascular prosthesis, according to claim 3, wherein said means for positioning include segments of wire connecting said annular loops defined by said first and second wire in order to keep them in substantially parallel planes.

5. Vascular prosthesis, according to claim 2, wherein ends of said first and second wire extending externally from said first end of said support are jointed to a cylinder for maneuvering said wires, said cylinder being mobile along an axis thereof, said axis being parallel to said axis of said support, thereby causing a sliding of said wire with respect to said support to obtain a first, second, third and fourth tract amplitude variation thereby allowing to expand and contract said expandable body and said tubular body.

6. Vascular prosthesis, according to claim 5, wherein said cylinder and a portion of said wire extending from said cylinder to said support are disposed externally to said tubular body.

7. Vascular prosthesis, according to claim 1, wherein said support is substantially cylindric.

8. Vascular prosthesis, according to claim 1, wherein said tubular body comprises a first portion disposed at said first end of said tubular body, and a second portion substantially coaxial with said first portion, said first portion being connected at an axial end of said second portion, said expandable body being connected to said first portion.

9. Vascular prosthesis, according to claim 1, wherein said wires are of harmonic stainless steel.

10. Vascular prosthesis for substitution or internal lining of a segment of a blood vessel of medium or large diameter, comprising a tubular body made of biocompatible material, said tubular body defining a lateral wall, a first and a second longitudinal end thereof and a longitudinal axis thereof;

a first radially expandable body and a second radially expandable body, said first and second expandable body being disposed substantially coaxial to said tubular body and perimetrically connected to said tubular body, each of said first and second expandable body comprising a support extending longitudinally along an axis between a first and a second longitudinal end thereof, said axis being substantially parallel to the axis of the tubular body, said support having a plurality of lateral holes, said plurality of lateral holes including at least a first lateral hole and a second lateral hole proximal to said first lateral hole, and at least a third lateral hole and a forth lateral hole proximal to said third hole, said third and fourth holes being longitudinally spaced with respect to said first and second holes; and at least one elastically flexible wire slidingly mounted on said support for radial expansion and contraction of said expandable body, said wire entering the support through said first longitudinal end thereof, said wire then coming out from the support through said first lateral hole and reentering the support through said third lateral hole so as to define a first tract of said wire inclined with respect to a plane perpendicular to said axis of said tubular body and a second tract of said wire in a plane perpendicular to said axis of said tubular body, said wire further coming out again from the support through said forth lateral hole and reentering the support through said second lateral hole thereby forming a third tract of said wire substantially in the same plan as the second tract, and a forth tract of said wire inclined with respect to a plan perpendicular to the axis of said tubular body, said second tract and said third tract forming substantially an annular loop, said wire coming out then from the support through said first longitudinal end thereof, thereby expansion and contraction of said tubular body is obtained when said wire slides with respect to said support, said wire being frictionally engaged to said support in said first, second, third and fourth lateral hole, said first and second expandable body being connected to said tubular body by repeated passages of said wire along said first, second, third and forth tract through the wall of said tubular body, thereby a radial expansion of said tubular body is obtained when said first and second expandable body are expanded, said first expandable body being connected to said tubular body in a first region of said tubular body proximal to said first longitudinal end of said tubular body and said second expandable body being connected to said tubular body in a second region of said tubular body proximal to said second end of said tubular body.

11. Vascular prosthesis, according to claim 10, wherein each of said first expandable body and said second expandable body comprises at least two wires, each of said at least two wires defining a first tract of said wire inclined with respect to a plane perpendicular to said axis of said tubular body, a second tract of said wire in a plane perpendicular to said axis of said tubular body, a third tract of said wire substantially in the same plan as the second tract, and a forth tract of said wire inclined with respect to a plan perpendicular to the axis of said tubular body, said second tract and said third tract forming substantially an annular loop, said first, second, third and forth tracts of said first wire being longitudinally spaced from and substantially parallel to said first, second, third and forth tracts of said second wire.

12. Vascular prosthesis, according to claim 11, comprising means for positioning said first wire in respect to said second wire.

13. Vascular prosthesis, according to claim 12, wherein said means for positioning include segments of wire connecting said annular loops defined by said first and second wire in order to keep them in substantially parallel planes.

14. Vascular prosthesis, according to claim 11, wherein ends of said first and second wire extending externally from said first end of said support are jointed to a cylinder for maneuvering said wires, said cylinder being mobile along an axis thereof, said axis being parallel to said axis of said support, thereby causing a sliding of said wire with respect to said support to obtain a first, second, third and fourth tract amplitude variation thereby allowing to expand and contract said expandable body and said tubular body.

15. Vascular prosthesis, according to claim 14, wherein said cylinder and a portion of said wires extending from said cylinder to said support are disposed externally to said tubular body.

16. Vascular prosthesis, according to claim 10, wherein said support is substantially cylindric.

17. Vascular prosthesis for substitution or internal lining of a segment of a blood vessel of medium or large diameter, comprising a tubular body made of biocompatible material, said tubular body defining a lateral wall, a first and a second longitudinal end thereof and a longitudinal axis thereof;

a first radially expandable body and a second radially expandable body, said first and second expandable body being disposed substantially coaxial to said tubular body and perimetrically connected to said tubular body, each of said first and second expandable body comprising a support extending longitudinally along an axis between a first and a second longitudinal end thereof, said axis being substantially parallel to the axis of the tubular body, said support having a plurality of lateral holes, said plurality of lateral holes including at least first lateral hole and a second lateral hole proximal to said first lateral hole, and at least a third lateral hole and a forth lateral hole proximal to said third hole, said third and fourth holes being longitudinally spaced with respect to said first and second holes; and at least one elastically flexible wire slidingly mounted on said support for radial expansion and contraction of said expandable body, said wire entering the support through said first longitudinal end thereof, said wire then coming out from the support through said first lateral hole and reentering the support through said third lateral hole so as to define a first tract of said wire inclined with respect to a plane perpendicular to said axis of said tubular body and a second tract of said wire in a plane perpendicular to said axis of said tubular body, said wire further coming out again from the support through said forth lateral hole and reentering the support through said second lateral hole thereby forming a third tract of said wire substantially in the same plan as the second tract, and a forth tract of said wire inclined with respect to a plan perpendicular to the axis of said tubular body, said second tract and said third tract forming substantially an annular loop, said wire coming out then from the support through said first longitudinal end thereof, thereby expansion and contraction of said tubular body is obtained when said wire slides with respect to said support, said wire being frictionally engaged to said support in said first, second, third and fourth lateral hole, said first and second expandable body being connected to said tubular body by repeated passages of said wire along said first, second, third and forth tract through the wall of said tubular body, thereby a radial expansion of said tubular body is obtained when said first and second expandable body are expanded, said first expandable body and said second expandable body being connected to said tubular body at said first longitudinal end of said tubular body, said support of said first expandable body being placed diametrically opposite to said support of said second expandable body.

18. Vascular prosthesis, according to claim 17, wherein each of said first expandable body and said second expandable body comprises at least two wires, each of said at least two wires defining a first tract of said wire inclined with respect to a plane perpendicular to said axis of said tubular body, a second tract of said wire in a plane perpendicular to said axis of said tubular body, a third tract of said wire substantially in the same plan as the second tract, and a forth tract of said wire inclined with respect to a plan perpendicular to the axis of said tubular body, said second tract and said third tract forming substantially an annular loop, said first, second, third and forth tracts of said first wire being longitudinally spaced from and substantially parallel to said first, second, third and forth tracts of said second wire.

19. Vascular prosthesis, according to claim 18, comprising means for positioning said first wire in respect to said second wire.

20. Vascular prosthesis, according to claim 19, wherein said means for positioning include segments of wire connecting said annular loops defined by said first and second wire in order to keep them in substantially parallel planes.

21. Vascular prosthesis, according to claim 18, wherein ends of said first and second wire extending externally from said first end of said support are jointed to a cylinder for maneuvering said wires, said cylinder being mobile along an axis thereof, said axis being parallel to said axis of said support, thereby causing a sliding of said wire with respect to said support to obtain a first, second, third and fourth tract amplitude variation thereby allowing to expand and contract said expandable body and said tubular body.

22. Vascular prosthesis, according to claim 21, wherein said cylinder and a portion of said wires extending from said cylinder to said support are disposed externally to said tubular body.

23. Vascular prosthesis, according to claim 17, wherein said support is substantially cylindric.

\* \* \* \* \*